United States Patent
Liu et al.

(10) Patent No.: US 12,424,306 B2
(45) Date of Patent: *Sep. 23, 2025

(54) TREE-BASED DATA EXPLORATION AND DATA-DRIVEN PROTOCOL

(71) Applicant: ABIOMED, Inc., Danvers, MA (US)

(72) Inventors: Chen Liu, Danvers, MA (US); Ahmad El Katerji, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/602,147

(22) Filed: Mar. 12, 2024

(65) Prior Publication Data

US 2024/0371487 A1 Nov. 7, 2024

Related U.S. Application Data

(63) Continuation of application No. 17/859,407, filed on Jul. 7, 2022, now Pat. No. 11,955,214, which is a
(Continued)

(51) Int. Cl.
*A61B 5/00* (2006.01)
*A61M 60/113* (2021.01)
(Continued)

(52) U.S. Cl.
CPC ........... *G16H 20/00* (2018.01); *A61B 5/7264* (2013.01); *A61B 5/7275* (2013.01);
(Continued)

(58) Field of Classification Search
CPC ............... A61B 5/7264; A61B 5/7275; A61M 2205/04; A61M 2205/3303;
(Continued)

(56) References Cited

U.S. PATENT DOCUMENTS 11,420,039 B2 * 8/2022 Liu ................. A61M 60/592
11,955,214 B2 * 4/2024 Liu ..................... G16H 20/40
(Continued)

FOREIGN PATENT DOCUMENTS

| CN | 1961321 A | 5/2007 |
| CN | 101400298 A | 4/2009 |
| CN | 103764843 A | 4/2014 |

OTHER PUBLICATIONS

International Search Report and Written Opinion for International Application No. PCT/US2019/054863 dated Jan. 15, 2020 (13 pages).
(Continued)

*Primary Examiner* — Jon Eric C Morales
(74) *Attorney, Agent, or Firm* — Botos Churchill IP Law LLP

(57) ABSTRACT

A method for providing a treatment recommendation to a physician for treating a patient is disclosed. The method comprises determining, from a processor in communication with a patient data repository, a first treatment recommendation based on a combination of selected patient demographics from the patient data repository applicable to the patient, and operational parameters of a plurality of ventricular assist devices (VADs) suitable for treating the patient, the first treatment recommendation having a first survival rate and comprising the use of a first VAD. The method then obtains a first signal from using the first VAD on the patient. The method then determines a second treatment recommendation based on the first signal and the first treatment recommendation, the second treatment recommendation having a second survival rate. The method then provides the second treatment recommendation to the physician if the second survival rate is higher than the first survival rate.

20 Claims, 6 Drawing Sheets

Related U.S. Application Data continuation of application No. 16/593,555, filed on Oct. 4, 2019, now Pat. No. 11,420,039.

(60) Provisional application No. 62/741,985, filed on Oct. 5, 2018.

(51) Int. Cl.
*A61M 60/17* (2021.01)
*A61M 60/178* (2021.01)
*A61M 60/205* (2021.01)
*A61M 60/216* (2021.01)
*A61M 60/295* (2021.01)
*A61M 60/50* (2021.01)
*A61M 60/515* (2021.01)
*A61M 60/538* (2021.01)
*A61M 60/592* (2021.01)
*G06N 20/20* (2019.01)
*G16H 20/00* (2018.01)

(52) U.S. Cl.
CPC .......... *A61M 60/113* (2021.01); *A61M 60/17* (2021.01); *A61M 60/178* (2021.01); *A61M 60/205* (2021.01); *A61M 60/216* (2021.01); *A61M 60/295* (2021.01); *A61M 60/50* (2021.01); *A61M 60/515* (2021.01); *A61M 60/538* (2021.01); *A61M 60/592* (2021.01); *G06N 20/20* (2019.01); *A61M 2205/04* (2013.01); *A61M 2205/3303* (2013.01); *A61M 2205/3331* (2013.01); *A61M 2205/50* (2013.01); *A61M 2210/125* (2013.01); *A61M 2230/30* (2013.01)

(58) Field of Classification Search
CPC ...... A61M 2205/3331; A61M 2205/50; A61M 2210/125; A61M 2230/30; A61M 60/00; A61M 60/113; A61M 60/17; A61M 60/178; A61M 60/205; A61M 60/216; A61M 60/295; A61M 60/50; A61M 60/515; A61M 60/538; A61M 60/592; G06N 20/20; G16H 20/00; G16H 20/40

See application file for complete search history.

(56) References Cited

U.S. PATENT DOCUMENTS

| | | |
|---|---|---|
| 2005/0261941 A1 | 11/2005 | Scarlat |
| 2006/0167334 A1 | 7/2006 | Anstadt et al. |
| 2007/0167687 A1 | 7/2007 | Bertolero et al. |
| 2011/0172545 A1 | 7/2011 | Grudic et al. |
| 2015/0339451 A1 | 11/2015 | Rolandelli et al. |
| 2018/0078159 A1 | 3/2018 | Edelman et al. |
| 2019/0192753 A1 | 6/2019 | Liu et al. |

OTHER PUBLICATIONS

Office Action from corresponding Chinese Patent Application No. 2019800650458 dated Sep. 16, 2023 (30 pages).
Office Action from corresponding Japanese Patent Application No. 2021-518526 dated Aug. 21, 2023 (16 pp.).
Office Action issued in corresponding Indian Patent Application No. 202117018795 dated Dec. 13, 2022, (6 pp.).
Office Action from corresponding Australian Patent Application No. 2019355192 dated May 23, 2024 (3 pp.).
Office Action from corresponding Israeli Patent Application No. 282011 dated Apr. 10, 2024 (4 pp.).
Office Action from corresponding Chinese Patent Application No. 2019800650458 dated Apr. 18, 2024 (12 pp.).
Office Action from corresponding Korean Patent Application No. 10-2021-7013478 dated Dec. 20, 2024 (16 pp.).

* cited by examiner

TREE-BASED DATA EXPLORATION AND DATA-DRIVEN PROTOCOL

CROSS-REFERENCE TO RELATED APPLICATIONS

The present application is a continuation of U.S. patent application Ser. No. 17/859,407, filed Jul. 7, 2022, now U.S. Pat. No. 11,955,214, which is a continuation of U.S. patent application Ser. No. 16/593,555, filed Oct. 4, 2019, now U.S. Pat. No. 11,420,039, which claims the benefit of the filing date of U.S. Provisional Patent Application No. 62/741,985, filed Oct. 5, 2018, the disclosures of which are hereby incorporated herein by reference.

BACKGROUND OF THE INVENTION

Acute and chronic cardiovascular conditions reduce quality of life and life expectancy. A variety of treatment modalities have been developed for treatment of the heart in such conditions, ranging from pharmaceuticals to mechanical devices and transplantation. Ventricular assist devices (VADs), such as heart pump systems and catheter systems, are often used in treatment of the heart to provide hemodynamic support and facilitate recovery. Some heart pump systems are percutaneously inserted into the heart and can run in parallel with the native heart to supplement cardiac output. Such heart pump systems include the Impella® family of devices by Abiomed, Inc. of Danvers, MA.

At present, the choice of a treatment plan using a VAD for patients with cardiovascular conditions is provided to a physician by a VAD controller, and is largely based on statistics of prior success with using the VAD for treating patients having similar conditions. Traditional data analytics are able to analyze a survival rate associated with the use of a VAD based on a single factor, e.g. a patient's gender or age. With the evolution of the types of myocardial conditions that a patient is susceptible to, treatment plans that are not streamlined to take into account additional factors that affect a patient's condition may deteriorate the patient's condition through treatment of the patient using a sub-optimal VAD.

BRIEF SUMMARY OF THE INVENTION

The methods and systems described herein use a tree-based predictive model to provide a physician with a treatment recommendation that is optimized to the patient. The method begins by determining, using a processor, a first treatment recommendation based on a combination of selected patient demographics obtained from a patient data repository that are applicable to the patient, and operational parameters of a plurality of ventricular assist devices (VADs) suitable for treating the patient, the first treatment recommendation having a first survival rate and comprising the use of a first VAD. The method then progresses to obtain a first signal from the first VAD through use of the VAD to treat the patient. The first signal is obtained from a controller in communication with the first VAD. The processor then determines a second treatment recommendation based on the first signal and the first treatment recommendation, the second treatment recommendation having a second survival rate. The processor then determines if the second survival rate is higher than the first survival rate, and, if so, provides the second treatment recommendation to the physician.

In some implementations, the method further comprises informing the physician to continue using the first VAD to treat the patient if the second survival rate is not higher than the first survival rate. Thus, if the processor determines that the second survival rate is equal to or lower than the first, the treatment of the patient using the first VAD is continued. In certain implementations, each VAD comprises at least one sensor for providing the first signal to the controller. The sensor may be any input transducer that is configured to convert patient data into electrical signals. In some implementation, the first signal comprises information that relates to the patient's vitals, such as, at least one of: Mean Arterial Pressure (MAP), Left Ventricular Pressure (LVP), Left Ventricular End-Diastolic Pressure (LVEDP), Pulmonary Arterial Wedge Pressure (PAWP), Pulmonary Capillary Wedge Pressure (PCWP), Pulmonary Artery Occlusion Pressure (PAOP), for example.

In certain implementations, if the second survival rate is determined to be higher than the first survival rate, the method further comprises treating the patient with the second treatment recommendation. The second treatment recommendation may comprise the use of at least one of the following for treating the patient: the first VAD, a second VAD, and no VAD. In some implementations, the second treatment recommendation may build upon the first treatment recommendation in that an additional VAD to use with the first VAD may be recommended. In certain implementations, the VAD comprises at least one of: an Impella® pump, an Extracorporeal Membrane Oxygenation (ECMO) pump, a balloon pump, and a Swan-Ganz catheter. The Impella® pump comprises any one of: Impella 2.5® pump, an Impella 5.0® pump, an Impella CPR pump, an Impella RP® pump and an Impella LD® pump. The aforementioned methods are used to for treating a patient in cardiogenic shock.

In some implementations, the first treatment recommendation is determined by a prediction model executed by the processor. In certain implementations, the prediction model is based on a machine learning algorithm comprising any one of: a bagging and random forest algorithm, a logistic regression algorithm, a classification decision tree algorithm, a deep learning algorithm, a naïve Bayes algorithm, and a support vector machines algorithm. In some implementations, the prediction model uses patient demographics that are applicable to the patient in its calculations. Such demographics include gender, age, region, duration of support, indication for use and insertion site. By using demographics that are patient specific, the resulting treatment recommendation provided to the patient is better suited to each patient, thus improving treatment efficacy.

In certain implementations, the processor may display the survival rate for each available VAD; and identifying the VAD with the highest survival rate. Additionally, the processor may display the combination of the selected patient demographics used for determining the survival rate using a branched-tree representation. Such feature combination trees provide the physician with a visualization of the features that have an influence on the recommended VAD (and associated survival rate) for treating the patient. In relation to the present disclosure, the survival rate comprises a probability of survival of a patient belonging to the combination of selected patient demographics when treated with a VAD.

In some implementations, the patient data repository comprises an Acute Myocardial Infarction Cardiogenic Shock (AMICS) database or a High-Risk Percutaneous Coronary Interventions (High-Risk PCI) database.

According to a second embodiment of the present disclosure, the methods and systems obtain data from a patient repository in which the data stored in the repository according to patient demographics. The method uses a processor to obtain data from the patient repository. The processor then determines at least one ventricular assist device (VAD) suitable for treating patient. The processor then determined, using a prediction model, a survival rate for each suitable VAD based on data from the patient data repository for a combination of selected patient demographics applicable to the patient. The processor then provides to a controller a recommended first VAD associated with the highest survival rate. The physician then uses the recommended first VAD to treat the patient.

In some implementations, the method further provides the physician with the survival rate for each suitable VAD for all combinations of the selected patient demographics applicable to the patient. In certain implementations, the processor also provides the physician with a survival rate for not using a VAD for each combination of the selected patient demographics applicable to the patient. In certain implementations, the first VAD may comprise at least one of: an Impella® pump, an Extracorporeal Membrane Oxygenation (ECMO) pump, a balloon pump, and a Swan-Ganz catheter. The Impella® pump may comprise any one of: Impella 2.5® pump, an Impella 5.0® pump, an Impella CP® pump, an Impella RP® pump and an Impella LD® pump. The patient demographics may comprise: age, gender, region, year of implantation, support device, duration of support, insertion site and ejection fraction.

In some implementations, the prediction model uses a machine learning algorithm to determine the survival rate. The machine learning algorithm may comprise any one of: a bagging and random forest algorithm, a logistic regression algorithm, a classification decision tree algorithm, a deep learning algorithm, a naïve Bayes algorithm, and a support vector machines algorithm. In certain implementations, the combination of the selected patient demographics follows a tree-model. The tree-model may have an order of any one of: two, three, four, five and six.

In some implementations, the method may further comprise displaying the survival rate for each available VAD, and identifying the VAD with the highest survival rate. In certain implementations, the method may further comprise displaying the combination of the selected patient demographics used for determining the survival rate using a branched-tree representation. The survival rate may comprise a probability of survival of a patient belonging to the combination of selected patient demographics when treated with a VAD. In some implementations, the patient data repository may comprise an Acute Myocardial Infarction Cardiogenic Shock (AMICS) database or a High-Risk Percutaneous Coronary Interventions (High-Risk PCI) database.

According to a third embodiment of the present disclosure, there is provided a system for providing a treatment recommendation to a physician for treating a patient. The system comprises at least one ventricular assist device (VAD) comprising a sensor. The system further comprises a processor in communication with the VAD, the processor configured to be in communication with an Acute Myocardial Infarction Cardiogenic Shock (AMICS) repository or a High-Risk Percutaneous Coronary Interventions (High-Risk PCI) repository. Further, the system comprises a controller in communication with the VAD and the processor, the controller being configured to perform a method according to any of the aforementioned embodiments.

According to a fourth embodiment of the present disclosure, there is provided a system for providing a treatment recommendation to a physician for treating a patient. The system comprises a processor and a controller configured to perform a method according to any of the aforementioned embodiments.

According to a fifth embodiment of the present disclosure, there is provided a computer program comprising computer executable instructions, which, when executed by a computing apparatus comprising a processor and a controller, causes the computing apparatus to perform a method according to any of the aforementioned embodiments.

According to a sixth embodiment of the present disclosure, there is provided a non-transitory computer-readable storage medium having stored thereon computer-readable code which, when executed by a computing apparatus comprising a processor and a controller, causes the computing apparatus to perform a method according to any of the aforementioned embodiments.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the methods and systems described herein, certain illustrative embodiments will be described. Although the embodiments and features described herein are specifically described for use in connection with survival rates for ventricular assist devices, it will be understood that all the components and other features outlined below may be combined with one another in any suitable manner and may be adapted and applied to other types of medical therapy having survival rates associated therewith.

The systems and methods described herein use predictive modeling to determine an optimal treatment recommendations for a patient in cardiogenic shock. Treatment recommendations may comprise the use of a single ventricular assist device (VAD) or a plurality of VADs, in combination with each other. The predictive model pulls in data and statistics from archived ventricular assist procedures performed in the past. Such patient data may be stored in a patient data repository such as an Acute Myocardial Infarction Cardiogenic Shock (AMICS) database or a High-Risk Percutaneous Coronary Interventions (High-Risk PCI) database, for example. The systems and methods use machine learning algorithms to predict survival rates when treating a patient with a VAD. To further customize the predictive model, patient demographics and operational parameters of the VAD are also included in the model using a selected tree-based combination of features. Here physicians are able to combine any number of patient demographics and/or device features to obtain a treatment recommendation with a realistic survival rate.

Additionally, real time patient data from use of a VAD on the patient may also be fed into the prediction model to further optimize the treatment recommendation. Such real time patient data may include, but is not limited to, Mean Arterial Pressure (MAP), Left Ventricular Pressure (LVP), Left Ventricular End-Diastolic Pressure (LVEDP), Pulmonary Arterial Wedge Pressure (PAWP), Pulmonary Capillary Wedge Pressure (PCWP), and Pulmonary Artery Occlusion Pressure (PAOP). VADs may comprise, but are not limited to, an Impella® pump, an Extracorporeal Membrane Oxygenation (ECMO) pump, a balloon pump, and a Swan-Ganz catheter. The Impella® pump may comprise an Impella 2.5® pump, an Impella 5.0® pump, an Impella CPR pump and an Impella LD® pump, all of which are by Abiomed, Inc. of Danvers, MA.

Figure 1:
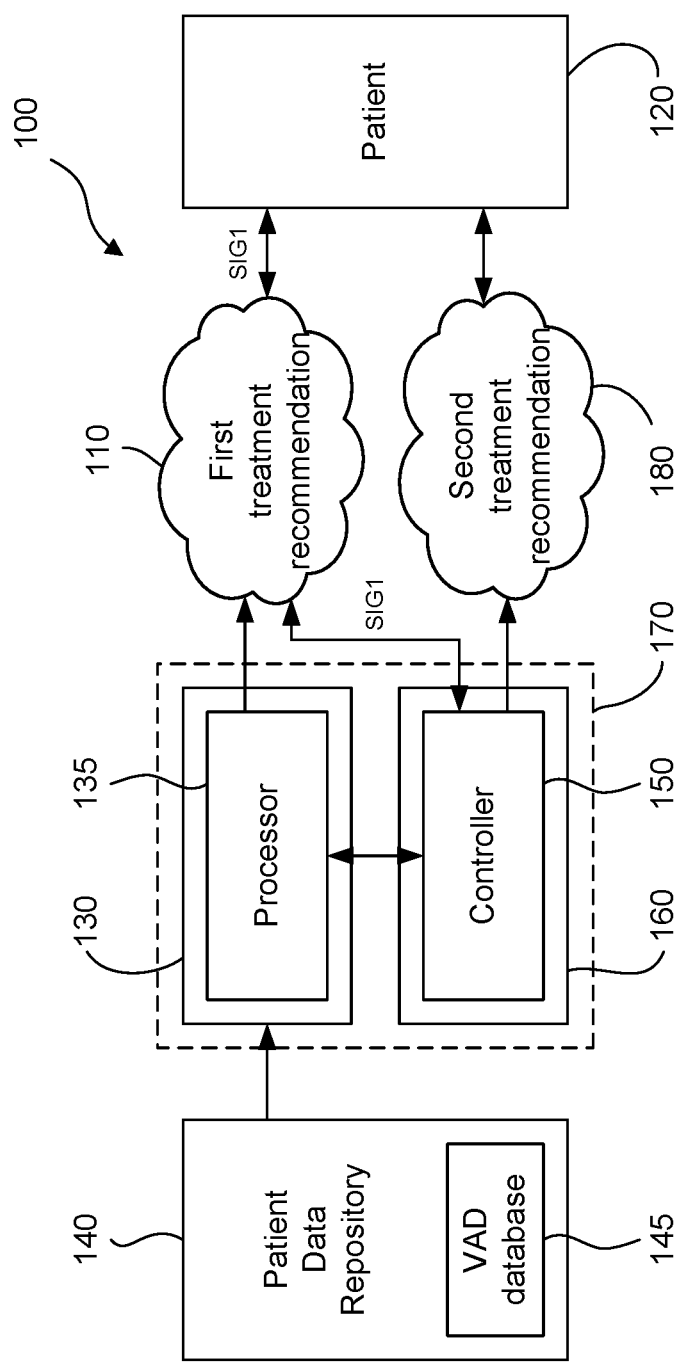
FIG. 1 shows an illustrative system according to an embodiment of the present disclosure.

FIG. 1 shows a block diagram of a system 100 for providing a first treatment recommendation 110 to a physician for treating a patient 120. The first treatment recommendation 110 comprises an indication to a physician as to the most appropriate VAD to use in view of the condition of the patient 120. VADs may comprise, but are not limited to, an Impella® pump, an Extracorporeal Membrane Oxygenation (ECMO) pump, a balloon pump, and a Swan-Ganz catheter. The Impella® pump may comprise an Impella 2.5® pump, an Impella 5.0® pump, an Impella CP® pump, an Impella RP® pump and an Impella LD® pump, all of which are by Abiomed, Inc. of Danvers, MA. The first treatment recommendation 110 is determined using a prediction model based on selected demographics applicable to the patient 120 and the operational parameters of all VADs suitable for the patient's condition. Here the survival rates of all VADs are then determined based on the selected demographics of the patient 120 and the operational parameters of the VADs. The VAD associated with the highest survival rate is then recommended to the physician. The indication may be by way of a display of the computing unit 130. In relation to FIG. 1, the first recommendation 110 comprises an indication to the physician to use a first VAD, having a first survival rate (SR1), for treating patient 120.

The system 100 also comprises a computing apparatus 130, such as a laptop, for example, in communication with a patient data repository 140. For the sake of brevity only a processor 135 of computing apparatus 130 is shown in FIG. 1. However, it will be understood that computing apparatus 130 also comprises other components typically associated with a computing apparatus, such as, for example, a volatile memory (e.g. a random-access memory RAM), a non-volatile memory (e.g. a read only memory ROM), a display, and connection busses that enable communication between these components, all of which are included in the present disclosure.

The computing apparatus 130 comprises a processor 135 that is able to perform operations on data using the prediction model. The computing apparatus 130 is in communication with a patient data repository 140 comprising patient data obtained from various medical institutions. According to certain embodiments of the present disclosure, patient data repository 140 may comprise an Acute Myocardial Infarction Cardiogenic Shock (AMICS) database or a High-Risk PCI database compiled and maintained by a CRM such as Salesforce.com, Inc. The patient data repository 140 stores data from treatment of acute myocardial infarction (AMI) patients, high-risk PCI patients, and patients in cardiogenic shock, for example. Patient data includes patient demographics such as, for example, gender, age and region. Patient data also includes data from previous treatments such as, for example, duration of support, indication for use, insertion site, treatment device, and ejection fraction. Exemplary AMICS data is shown in Table 1. In some instances, the patient data repository 140 also comprises a database 145 of available VADs and their associated operation parameters.

Processor 135 of processing unit 130 is also in communication with a controller 150 which controls the operation of any VAD used to treat the patient 120. Each VAD comprises a sensor that collects data from the patient while the VAD is in use, and transmits this data as signals (such as SIG1 in FIG. 1) to the controller 150. Such data may include, but is not limited to, Mean Arterial Pressure (MAP), Left Ventricular Pressure (LVP), Left Ventricular End-Diastolic Pressure (LVEDP), Pulmonary Arterial Wedge Pressure (PAWP), Pulmonary Capillary Wedge Pressure (PCWP), and Pulmonary Artery Occlusion Pressure (PAOP). The first VAD of the first treatment recommendation 110 is connected to the controller 150, and transmits a first signal (SIG1) to the controller 150. In some embodiments, controller 150 comprises an Automatic Impella® Controller (AIC) by Abiomed, Inc. of Danvers, MA. Controller 150 may be housed in a servicing hub 160 that may comprise other components to ensure that the respective VADs connected thereto are in operational order. In certain embodiments, the processor 130, the processing unit 135, the controller 150 and the servicing hub 160 may be housed in a work station 170. The work station 170 may further comprise a display (not shown) to indicate a treatment recommendation to the physician.

TABLE 1

Exemplary AMICS data

| | Ejection Fraction | Procedure Outcome | Procedure Outcome_1 | Support Status at End of Case | Swan-Ganz | ECMO Used |
|---|---|---|---|---|---|---|
| 18814 | 40 | Survived | Survived | Explanted in Cath Lab | | |
| 18815 | * | | | Explanted in Cath Lab | | Not Used |
| 18816 | 15 | Survived | Survived | Explanted in Cath Lab | | |
| 18817 | * | Unknown | Unknown | Unknown | | |
| 18818 | * | Survived | Survived | Explanted in Cath Lab | | |
| 18819 | 10 | Survived | Survived | On Support/Sent to Unit | | |
| 18820 | * | Survived | Survived | Explanted in Cath Lab | | |
| 18821 | 10 | | | Expired in Cath Lab | | |

TABLE 1-continued

Exemplary AMICS data

| | Ejection Fraction | Procedure Outcome | Procedure Outcome_1 | Support Status at End of Case | Swan-Ganz | ECMO Used |
|---|---|---|---|---|---|---|
| 18822 | 10 | | | Explanted in Cath Lab | | |
| 18823 | 10 | | | Explanted in Cath Lab | | Not Used |
| 18824 | 15 | | | Explanted in Cath Lab | | Not Used |
| 18825 | 15 | | | Explanted in Cath Lab | | Not Used |
| 18826 | * | | | Unknown | | Unknown |
| 18827 | * | Survived | Survived | On Support/Sent to Unit | | |
| 18828 | 15 | Survived | Survived | Explanted within 3 Hours of Admission to ICU | | |
| 18829 | 35 | | | Explanted in Cath Lab | | Not Used |
| 18830 | * | | | Explanted in Cath Lab | | Not Used |
| 18831 | 20 | Survived | Survived | Explanted within 3 Hours of Admission to ICU | | |
| 18832 | * | Survived | Survived | Explanted in Cath Lab | | |
| 18833 | 10 | | | Explanted in Cath Lab | No | Not Used |
| 18834 | * | | | Expired within 3 Hours of Admission to ICU | | |
| 18835 | * | Survived | Survived | Explanted in Cath Lab | | |
| 18836 | * | | | Explanted within 3 Hours of Admission to ICU | | |
| 18837 | 5 | | | Explanted within 3 Hours of Admission to ICU | | Not Used |
| 18838 | * | Survived | Survived | On Support/Sent to Unit | | ECMO added to Impella |
| 18839 | 25 | | | Explanted in Cath Lab | | |

According to certain embodiments of the present disclosure, the controller 150 may additionally provide the physician with an indication of a second treatment recommendation after the physician uses the first VAD to treat the patient 120. Here, the transmitted first signal SIG1 from the first VAD is received by the controller 150. The controller 150 then determines a second treatment recommendation comprising the use of at least a second VAD using a comparison model based on SIG1, the operational parameters of the first VAD, and the operational parameters of all suitable VADs in the database 145. The survival rates of all suitable VADs are also determined and the VAD with the highest survival rates is selected as the second VAD. A second survival rate (SR2) of the second VAD is also determined by the controller 150 from the AMICS database 140.

The controller 150 then compares the first survival rate SR1 with that of the second survival rate SR2. If the second survival rate SR2 is higher than the first survival rate SR1, i.e. SR2>SR1, the second recommendation is provided to the physician, via the display on the workstation 170. The second recommendation may comprise an indication to the physician to use the second VAD in place of the first VAD to treat the patient 120. The second recommendation may also comprise an indication to the physician to use a combination of VADs selected from the database 145. The VADs used in the combination may comprise VADs other than the first VAD, or at least one second VAD in addition to the first VAD. Further, the second recommendation may comprise the use of no VAD at all, i.e. the second recommendation may be an indication to the physician to stop treating the patient with any VAD. If the second survival rate SR2 is not higher than the first survival rate SR1, i.e. SR2≤SR1, the controller 150 indicates to the physician that no change to the first treatment recommendation should be made.

Figure 2:
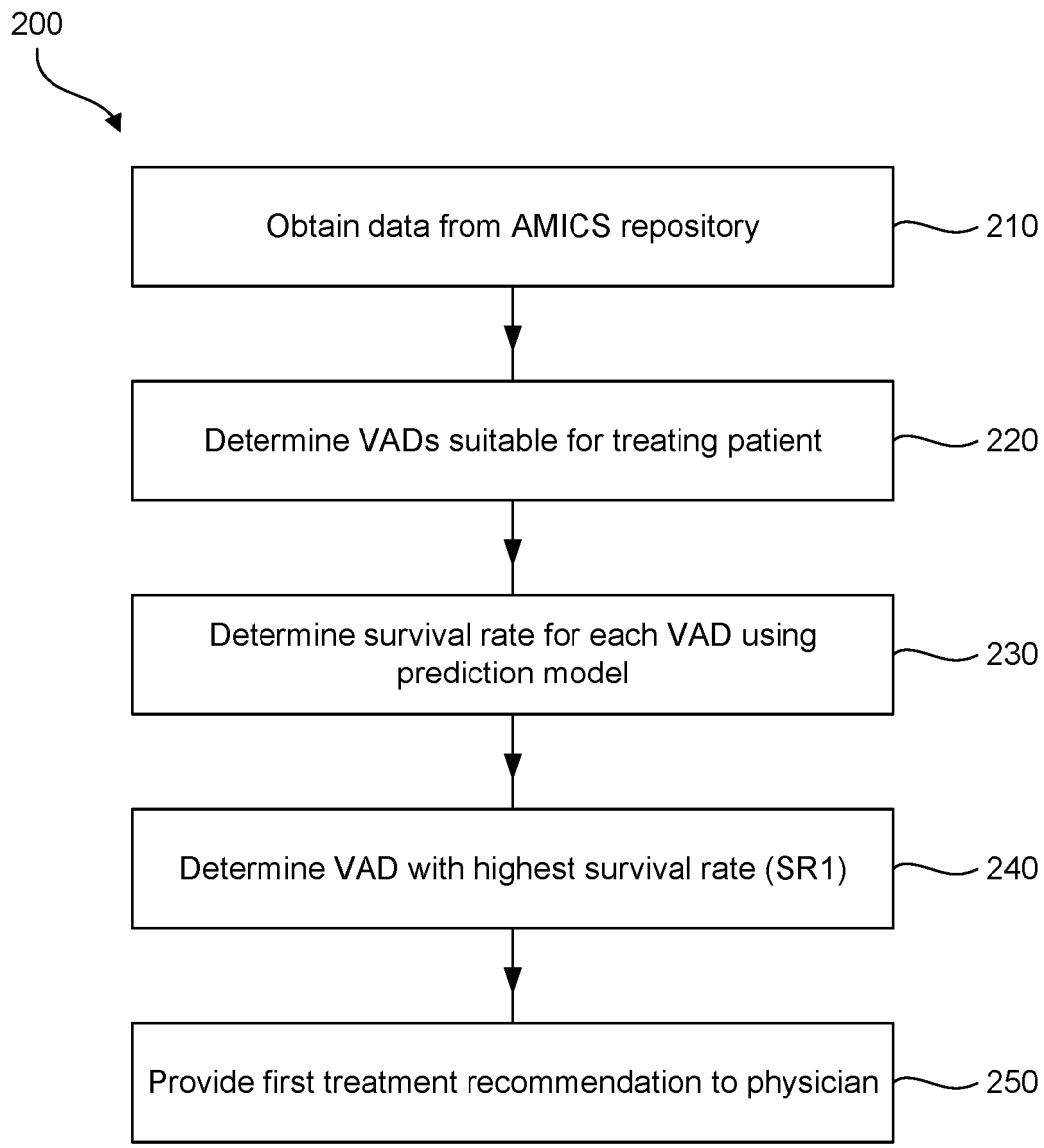
FIG. 2 shows an illustrative flowchart of a method for providing a treatment recommendation to a physician for treating a patient according to an embodiment of the present disclosure.

FIG. 2 shows a flowchart of a method 200 of providing a first treatment recommendation to a physician for treating a patient in cardiogenic shock according to an embodiment of the present disclosure. The method 200 is based on the features of the system 100 as described in the foregoing in relation to FIG. 1. The method begins at step 210 in which a processor 135 of a computing unit 130 accesses a patient data repository 140. In some embodiments, the repository 140 may comprise an AMICS or High-Risk PCI database which includes a VAD database 145. The processor 135 then determines, in step 220, VADs suitable for treating the patient. Such suitability may be based on clinical indications of the patient, and the operational parameters of the VAD obtained from the patient data repository 140. The processor 135 therefore determines a shortlist of suitable VADs from the patient data repository 140 for treating the patient in step 220.

In step 230 of the method, the processor 135 uses a prediction model to determine a survival rate for each VAD in the shortlist from step 220. The prediction model is based on a machine learning algorithm, which, in turn includes, but is not limited to, a bagging and random forest algorithm, a logistic regression algorithm, a classification decision tree algorithm, a deep learning algorithm, a naïve Bayes algorithm and a support vector machines algorithm, the details of which are omitted from this disclosure for brevity.

For example, the logistic regression algorithm is based on an equation used to represent the predictive model with coefficients learned from training data. A representation of the model may be stored in a memory of the computing unit 130 as a series of the coefficients, each corresponding to a weight indicative of a relative importance of a particular feature (e.g. a particular patient demographic), and can be used to calculate a probability, which is then translated as the survival rate of a patient. The probability may be calculated as $(1+\exp(-x))-1$, wherein x is equal to $\alpha*\text{Feature\_}\alpha + \beta*\text{Feature\_}\beta + \gamma*\text{Feature\_}\gamma + \ldots$ for any number of features (Feature_$\alpha$, Feature_$\beta$, Feature_$\gamma$) and associated coefficients ($\alpha$, $\beta$, $\gamma$).

In another example, the decision tree algorithm uses a decision tree as a predictive model to go from observations about an item to conclusions about the item's target value. Tree depth may be a hyper-parameter in decision tree learning. A hyper-parameter is a value that cannot be estimated from data used in the model. Hyper-parameters are often used to help estimate model parameters and can be tuned for a given predictive modeling problem. Precision may be used as a performance metric of a predictive model. By determining the maximum precision of the decision tree through tuning hyper-parameters such as tree depth, the system can provide an optimized machine learning model, and therefore better provide a prediction (such as the survival rate). Receiver Operating Characteristic (ROC) and Area Under Curve (AUC) may also be used as metrics to compare prediction algorithms.

In step 240 of the method, the processor 135 compares the survival rate obtained for each VAD and determines the VAD with the highest survival rate. In step 250, the processor 135 provides a first treatment recommendation to the physician, via an indication on the display connected to the processor, to use the VAD with the highest survival rate for treating the patient. The provision of the first treatment recommendation in the method 200 of FIG. 2 customizes the first treatment recommendation to the needs of the patient using the tree-based data driven protocol as described in the foregoing. By fine customizing the treatment to the patient's demographics, the most effective treatment plan (based on historical analysis of data in data repository 140, for example) with the best survival rate is provided to the patient, thereby ensuring effective treatment of patients in cardiogenic shock.

Figure 3A:
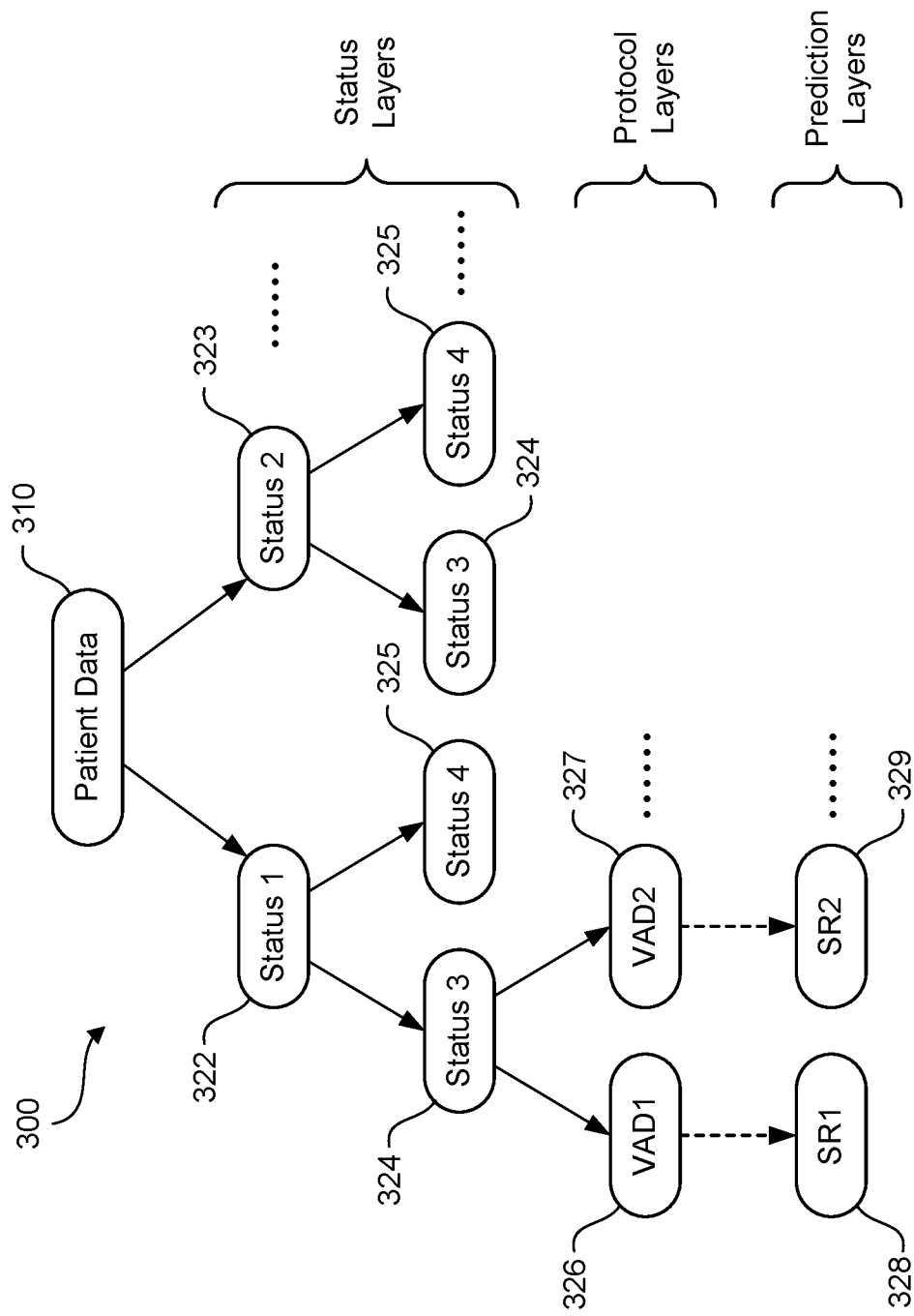
FIGS. 3A-3C show illustrative tree-diagrams with patient demographic factors that contribute to the survival rate for use of a VAD on a patient.

FIG. 3A illustrates a patient demographic/feature combination tree according to an embodiment of the present disclosure. The tree 300 illustrates how various types of features and treatments can be combined to determine the treatment with the highest predicted survival rate. The features are determined from the attributes of the data 310 stored in the data repository 140. As seen from Table 1, the data stored in the repository 140 may have various attributes such as gender, age, ejection fraction, type of catheter used (e.g. Swan-Ganz), and type of pump used (e.g. ECMO). The attributes of the data that relate to the demographics of the patient are used in the combination tree 300 as status layer features, such as features 322-325. Status layer features are features that relate to the patient and cannot be changed, i.e. the status layer features do not have adjustable values. Examples of status layer features include, but are not limited to, gender, age and ejection fraction. The repository 140 also stores data that relates to the type of VADs available. The features of such VADs are used in the combination tree 300 as protocol layer features, such as features 326-327. Protocol layer features are physician selectable options of the VAD that are facilitate controlled operation of the VAD. The protocol layer features have values associated with them that can be specified by the physician. Examples of protocol layer features include, but are not limited to, rotor speed and flow rate.

The selected status layer features and selected protocol layer features pull patient data 310 from the data repository 140, such that said pulled data can be used in a prediction model to determine and provide the physician with predicted survival rates 328-329 for each respective combination of selected features 322-327. The predicted survival rates 328-329 are provided in a prediction layer in tree 300. In some embodiments, the prediction model may identify the combination of features 322-327 that gives the highest predicted survival rate. The combination of features 322-327 that relate to the highest predicted survival rate are provided to the physician as a treatment recommendation. The treatment recommendation may be provided to the physician on a monitor. The combination of features that make up the treatment recommendation may be presented to the physician in a feature combination tree, such as tree 310 in FIG. 3A.

It will be understood that cardiac assist technologies develop over time. Further, increased exposure and use of VADs by physicians improve their impact on a patient's condition (e.g. once a physician is better trained at using a VAD, the effect the use of the VAD has on a patient with a particular condition would be seen in the patient data—for example the ejection fraction for a particular VAD may increase). According to an embodiment of the present disclosure, in order to cater to such factors, the prediction model may specify a date range when pulling patient data 310 from the data repository 140. In such situations, the prediction model effectively weighs the data and only uses patient data 310 from the repository 140 that falls within the specified date range. While such data weightage is exemplified in the forgoing by way of a date range, other factors may be considered when weighing the pulled data 310.

Figure 3B:
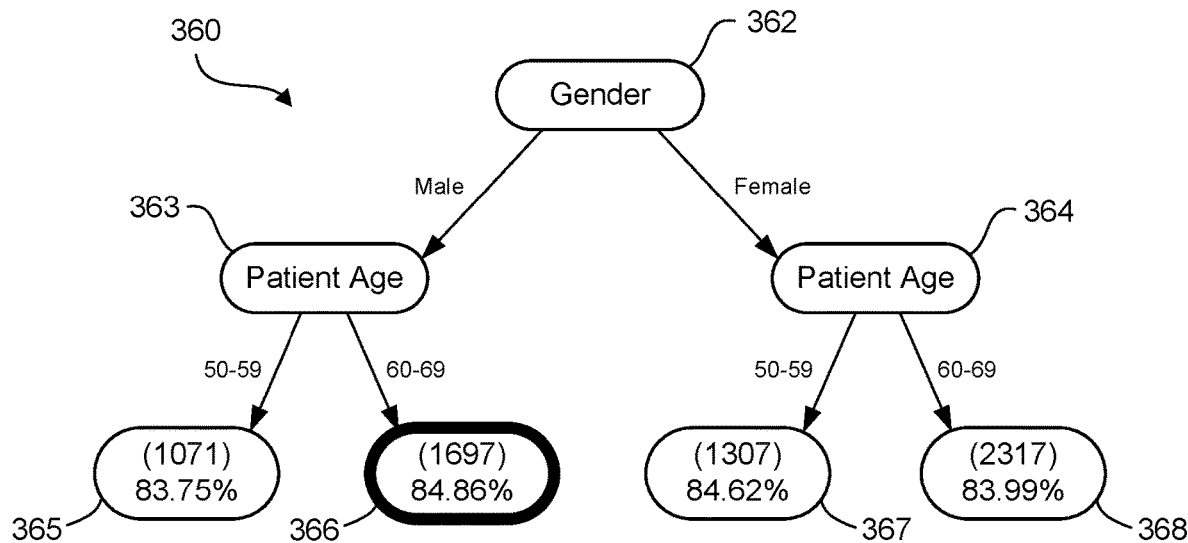

FIG. 3B illustrates an exemplary feature combination tree 360 of various types of patient demographic data used in the predictive model according to an embodiment of the present disclosure. As previously described, the patient demographic data is stored in the patient data repository 140 and may comprise, for example, gender, age and region. Tree 360 illustrates the combination of the patient's gender 362 and age 363, 364. These combinations are for the use of a specific type of VAD (e.g. Impella® 2.5 pump, for example). Based on data extracted from the patient data repository 140, feature 362 has values 'male' and 'female', and features 363, 364 have values '50-59' and '60-69'. Thus, based on the tree-based data combination illustrated in FIG. 3B, using the data in the patient data repository 140 for the selected patient demographic data, and a machine learning algorithm (as detailed above), the survival rates 365-368 for each combination of the tree 360 is as illustrated in FIG. 3B. FIG. 3B shows that male patients in the age range of 60-69, in which a particular VAD has been implanted (e.g. an Impella® 2.5 pump), have the highest survival rate of 84.86%. The data used for determining the survival rate in FIG. 3B is based on 1,071+1,697+1,307+2,317=6,392 records in the patient data repository 140 which have features 362-364. The example in FIG. 3B illustrates the influence of the combination of features of patient data on the survival rate as determined by the prediction model.

Figure 3C:
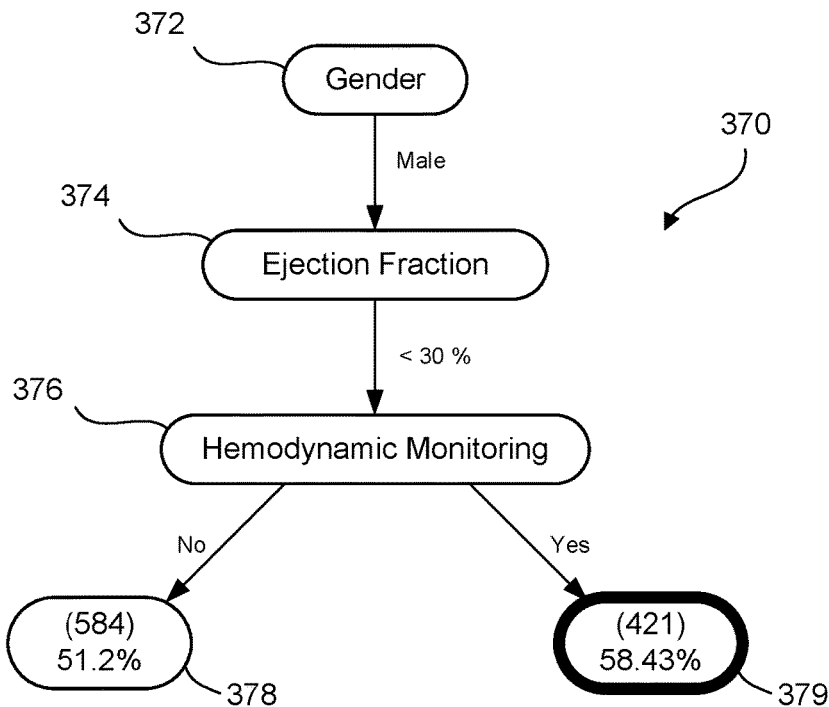

A further example of the tree-based data-driven method of the present disclosure is illustrated in the feature combination tree 370 shown in FIG. 3C. Tree 370 illustrates the combination of three types of patient data: gender 372, ejection fraction 374, and the availability of hemodynamic monitoring 376. The availability of hemodynamic monitoring is dependent on the type of VAD used. For example, Swan-Ganz catheters are known to have pressure sensors available that facilitate such hemodynamic monitoring. The selected patient demographics for the combination in FIG. 3C are: male, ejection fraction of less than 30%, and hemodynamic monitoring. Based on the tree-based data combination illustrated in FIG. 3C, using the data in the patient data repository 140 for the selected patient demographic data, and a prediction model (as detailed above), the survival rates 378-379 for this specific combination of patient demographics is as illustrated in FIG. 3C. The highest survival rate is 58.43% for the use of VADs capable of hemodynamic monitoring on male patients with an ejection fraction of less than 30%. The treatment recommendation to the physician is therefore: use a VAD capable of hemodynamic monitoring (e.g. a Swan-Ganz catheter) for male patients with for an ejection fraction of less than 30%. For completeness, branch 378 in the tree 370 indicates the survival rate for using a VAD that is not capable of hemodynamic monitoring on a male patient for an ejection fraction of less than 30%. The data used for determining the survival rate in FIG. 3C is based on 584+421=1,005 records in the patient data repository 140 which have features 372, 374 and 376. A graphical representation of feature combination trees 360 and 370 may also be displayed to the physician alongside the first and/or second treatment recommendation, on a monitor, for example.

Figure 4A:
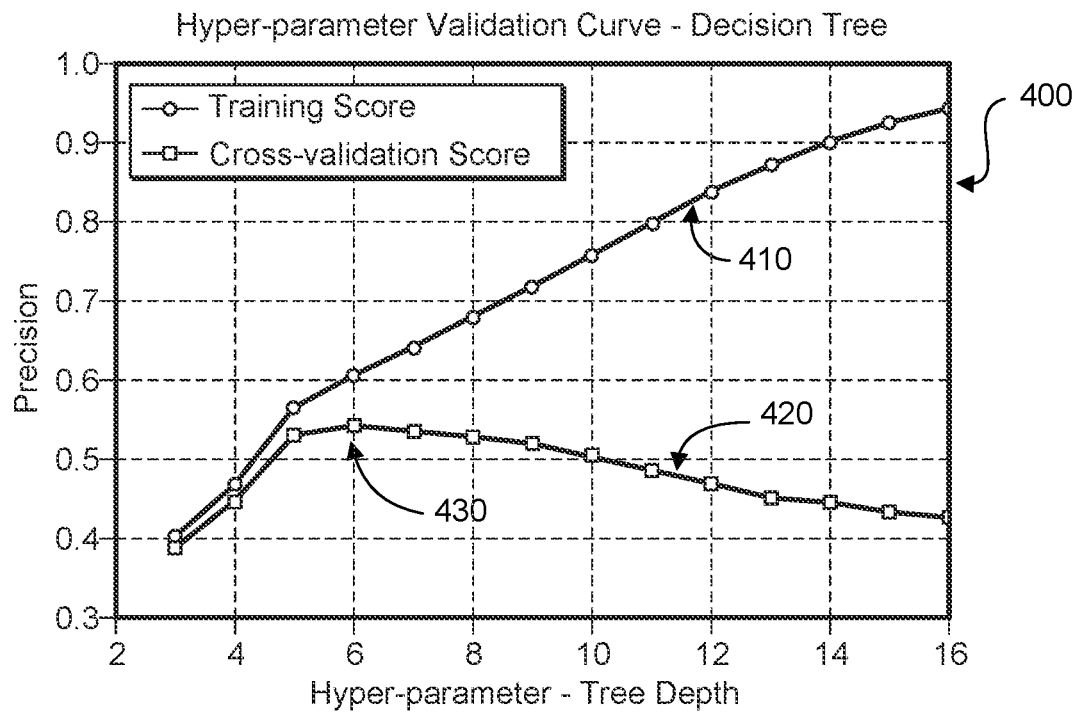
FIG. 4A illustrates precision of the prediction model based on the order/depth of the tree diagram of the method of the present disclosure.

FIG. 4A illustrates a data plot 400 for precision optimization of the prediction model using a decision tree algorithm. As previously described, the decision tree algorithm may use a hyper-parameter as the tree depth. By determining the maximum precision of the decision tree algorithm through tuning hyper-parameters such as tree depth, the system can provide an optimized machine learning model, and therefore better provide a prediction (such as the survival rate). As shown in FIG. 4A, when we change the hyper-parameter (tree depth) to a large value, the decision tree algorithm is able to capture all the noise of the training data. This results in a high training score, as can be seen by the line plot 410 in FIG. 4A. However, at such large tree depths, the model overfits the data and is not generalized enough. As a consequence, the cross-validation score deteriorates, as can be seen by the line plot 420 in FIG. 4A. For the decision tree algorithm, if the tree is too shallow, e.g. a tree depth of 2 or 3, the prediction model is too simple and is unable to make any prediction that are correct, as shown in FIG. 4A where both the training and cross-validation scores are low. Thus, the optimal tree depth for the decision tree algorithm is one which maximizes the cross-validation score and the training score. This occurs at the peak of the cross-validation curve (point 430), at a tree depth of 6 as shown in FIG. 4A.

Figure 4B:
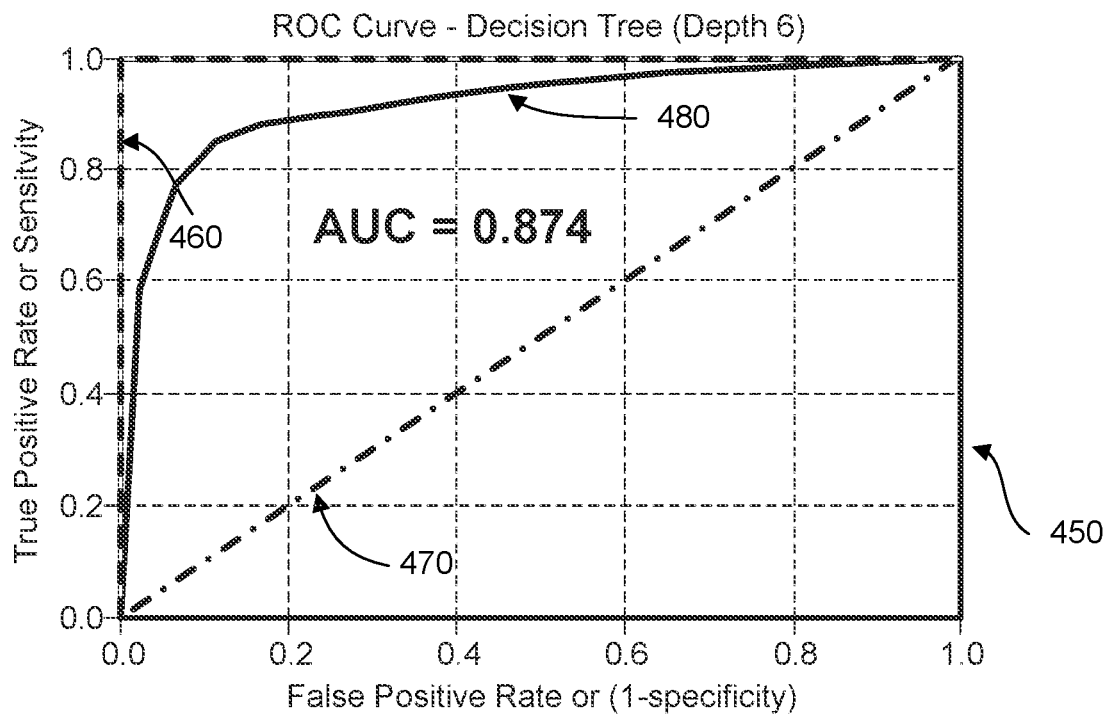
FIG. 4B illustrates output of the prediction model with an optimized tree depth.

In machine learning, a false positive is a machine indicated result which incorrectly indicates that a condition or attribute is present. Similarly, a false negative is one in which the machine indicated result incorrectly identifies that a condition or attribute is absent. Ideally the prediction model should predict a survival rate for a VAD that matches up with the real survival rate when using the VAD on a patient. However, as with most machine learning, there is no perfect model in real life and so when evaluating machine learning models, one trades off false positive with false negative, and vice versa. The ROC curve for a tree depth of 6 is shown in FIG. 4B. The ROC curve 450 scans through false positive rate from 0 to 100% and checks what is the true positive rate given by the model. The line plot 460 is the ideal with an area under curve AUC of 100%, while the line plot 470 is based on a random model with an AUC of 50%. Any reasonable prediction model should stay in between line plot 460 and line plot 470. For the decision tree algorithm discussed above in relation for FIG. 4A, the true positive rate is shown by line plot 480 and the AUC is 87.4% showing a good predictive power of the prediction model when using a decision tree algorithm. For clarity, the decision tree algorithm is one of many machine learning algorithms that can be used as the prediction model according to the present disclosure. The feature combination trees in FIGS. 3B and 3C are separate from the prediction model and provides the physician with an illustration of how selected features and/or patient demographics are combined in the decision model.

Figure 5:
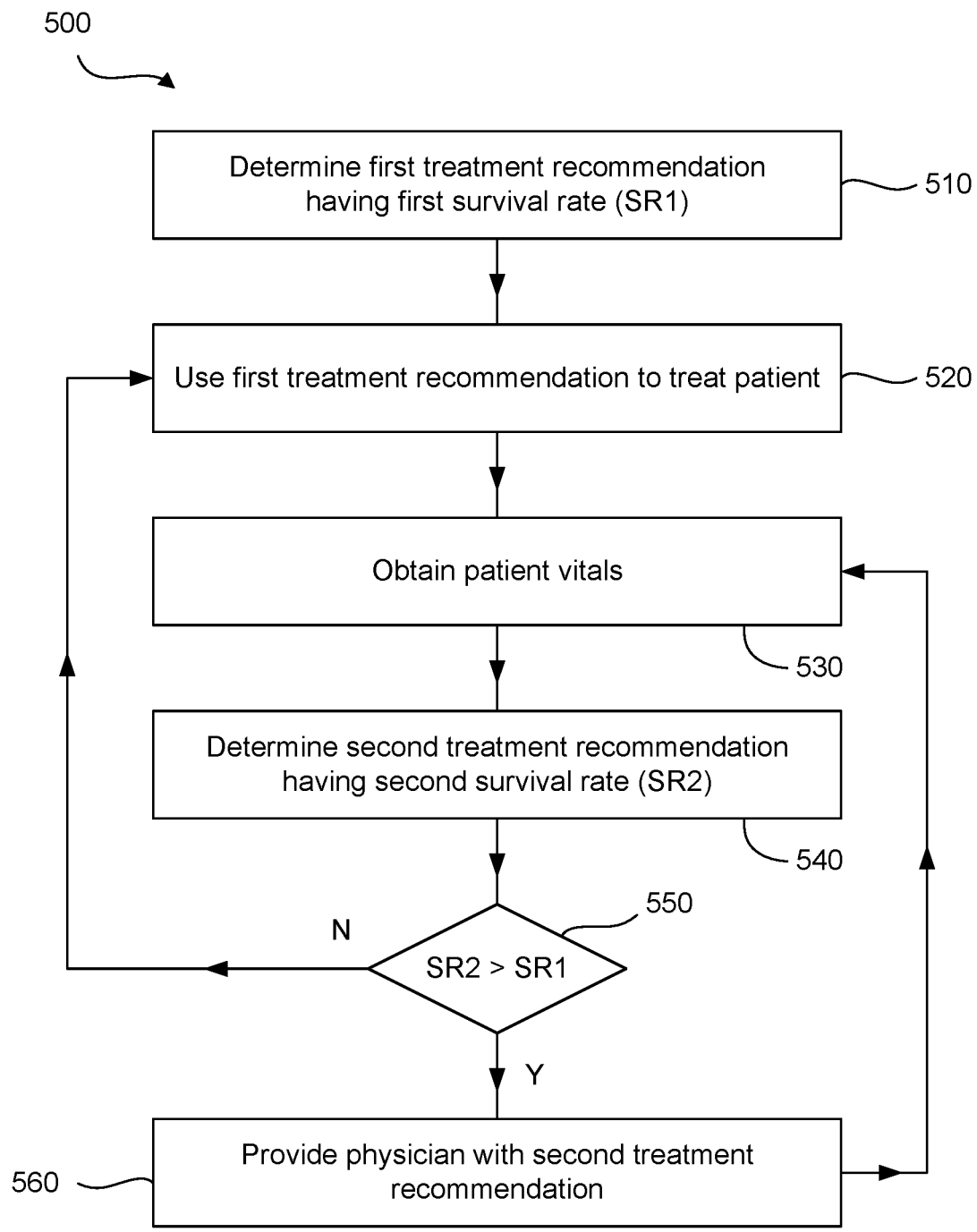
FIG. 5 shows an illustrative flowchart of a method for providing a second treatment recommendation to a physician for treating a patient according to a further embodiment of the present disclosure.

FIG. 5 shows a flowchart of a method 500 of providing a second treatment recommendation to a physician for treating a patient in cardiogenic shock according to a further embodiment of the present disclosure. The method 500 is based on the features of the system 100 as described in the foregoing in relation to FIG. 1. The method 500 works off step 250 of method 200 in FIG. 2 in which the physician is provided with a first treatment recommendation comprising the use of a first VAD having a first survival rate (SR1). Method 500 begins at step 510 in which the first treatment recommendation is determined by the processor 135. As previously mentioned in relation to FIG. 2, the processor 135 accesses the patient data repository 140 and determines VADs suitable for treating the patient. Such suitability may be based on clinical indications of the patient, and the operational parameters of the VAD obtained from patient data repository 140, for example. The processor 135 determines a first shortlist of suitable VADs from the patient data repository 140 for treating the patient and uses a prediction model to determine a survival rate for each VAD in the first shortlist. As previously mentioned, the prediction model is based on a machine learning algorithm, which, in turn includes, but is not limited to, a bagging and random forest algorithm, a logistic regression algorithm, a classification tree algorithm, a deep learning algorithm, a naïve Bayes algorithm and a support vector machines algorithm. The VAD with the highest survival rate is used for the first treatment recommendation, termed the first VAD having a first survival rate (SR1).

The physician is informed of the first treatment recommendation via a display unit connected to the processor 135, and uses the first VAD to treat the patient (step 520). The feature combination tree (e.g. tree 300 and 350) may also be displayed. Each VAD comprises a sensor that collects data from the patient while the VAD is in use (step 530), and transmits this data as signals (SIG1) to the controller 150 and the processor 135. In some embodiments of the present disclosure, the collection of patient data or patient vitals, termed a patient vitals check, is done at predetermined intervals of time during the period in which the patient is being treated with the first VAD. As previously mentioned, such data may include, but is not limited to, Mean Arterial Pressure (MAP), Left Ventricular Pressure (LVP), Left Ventricular End-Diastolic Pressure (LVEDP), Pulmonary Arterial Wedge Pressure (PAWP), Pulmonary Capillary Wedge Pressure (PCWP), and Pulmonary Artery Occlusion Pressure (PAOP).

In step 540, the processor 135 determines a second shortlist of VADs from the patient data repository 140 that are suitable in treating the patient based on the patient data contained in SIG1. As will be appreciated, as the patient is treated with the first VAD, the patient's vitals may change and therefore the patient data in SIG1 may be different to the clinical indications of the patient used in determining the first treatment recommendation. Thus, the VADs in the second shortlist may be different to those in the first shortlist. As with the VADs in the first shortlist, the processor 135 uses a prediction model to determine a survival rate for each VAD in the second shortlist. The prediction model is based on a machine learning algorithm, which may include but is not limited to, a bagging and random forest algorithm, a logistic regression algorithm, a classification and regression tree algorithm, a deep learning algorithm, a decision tree algorithm, a naïve Bayes algorithm, a support vector machines algorithm and a vector quantization algorithm.

The VAD with the highest survival rate, termed the second VAD, is determined (step 540) and the processor 135 compares its survival rate (SR2) to that of the first VAD (SR1), in step 550. If SR2>SR1, the second VAD is used in a second treatment recommendation to the physician (step 560). The physician is informed of the second treatment recommendation via a display unit connected to the processor 135. If SR2≤SR1, the second treatment recommendation is not provided to the physician, and, instead, an indication is made to the physician (via the monitor) to continue using the first treatment recommendation and continue treating the patient with the first VAD, step 520, until the next patient vitals check. After the second treatment recommendation is provided to the physician, the method 500 may continue to perform patient vitals checks to further refine the treatment process, as shown in FIG. 5.

The provision of the second treatment recommendation in the method 500 of FIG. 5 further customizes the first treatment recommendation to the progress of the patient undergoing said treatment using the tree-based data driven protocol as described in the foregoing. Such further customization ensures that the treatment recommendation with the highest survival rate is provided to the physician for the further treatment of patient. By fine turning the treatment to the progress of the patient, the treatment of patients in cardiogenic shock will be more effective.

In certain embodiments, feature combination trees are also displayed on a monitor attached to the processor running the decision model. These feature combination trees are similar to those depicted in FIGS. 3B and 3C. Such feature combination trees provide the physician with a visualization of the features that have an influence on the recommended VAD for treating the patient.

In certain embodiments, the second treatment recommendation may comprise the use of a single second VAD or a plurality of second VADs, in combination with each other. For example, the first treatment recommendation may comprise the use of a balloon pump while the second treatment recommendation may comprise the use of an ECMO pump in combination with a Swan-Ganz catheter. As a further example, the first treatment recommendation may comprise the use of an Impella 2.5® pump while the second treatment recommendation may comprise the continued use of the Impella 2.5® pump in combination with a balloon pump. In such situations, the second shortlist will generate two VADs associated with the highest survival rates. In certain embodiments of the present disclosure, the processor can be configured to ascertain the top n VADs with the higher survival rate, where n≥1. The survival rates of these n VADs are then compared to that of the first VAD in step 550 of method 500 in FIG. 5. According to some embodiments of the present disclosure, the second treatment recommendation may be to stop the use of any VAD, as in the 'No' option 391 in FIG. 3, whereby the 'No VAD' option for a first VAD gives the highest survival rate.

In relation to the present disclosure, a computer-readable medium may comprise a computer-readable storage medium that may be any tangible media or means that can contain or store the instructions for use by or in connection with an instruction execution system, apparatus, or device, such as a computer as defined previously, for performing any of the methods described herewith.

According to various embodiments of the present disclosure, a computer program may be implemented in a computer program product comprising a tangible computer-readable medium bearing computer program code embodied therein which can be used with the processor for the implementation of the functions or methods described above.

Reference to "computer-readable storage medium", "computer program product", "tangibly embodied computer program" etc., or a "processor" or "processing circuit" etc. should be understood to encompass not only computers having differing architectures such as single/multi-processor architectures and sequencers/parallel architectures, but also specialized circuits such as field programmable gate arrays FPGA, application specify circuits ASIC, signal processing devices and other devices. References to computer program, instructions, code etc. should be understood to express software for a programmable processor firmware such as the programmable content of a hardware device as instructions for a processor or configured or configuration settings for a fixed function device, gate array, programmable logic device, etc.

By way of example, and not limitation, such "computer-readable storage medium" may mean a non-transitory computer-readable storage medium which may comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a "computer-readable medium". For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that "computer-readable storage medium" and data storage media do not include connections, carrier waves, signals, or other transient media, but are instead directed to non-transient, tangible storage media. Disk and disc, as used herein, include compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of "computer-readable medium".

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

If desired, the different steps discussed herein may be performed in a different order and/or concurrently with each other. Furthermore, if desired, one or more of the above-described steps may be optional or may be combined.

The foregoing is merely illustrative of the principles of the disclosure, and the apparatuses can be practiced by other than the described implementations, which are presented for purposes of illustration and not of limitation. It is to be understood that the methods disclosed herein, while shown for use in automated ventricular assistance systems, may be applied to systems to be used in other automated medical systems.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method comprising:
obtaining training data from a data repository, wherein the training data comprises patient data and operational parameters of a plurality of ventricular assist devices (VADs), and wherein the data repository comprises data from treatment of acute myocardial infarction (AMI) patients, high-risk percutaneous coronary interventions (PCI) patients, or patients in cardiogenic shock;
training a prediction model with the training data, wherein the trained prediction model is configured to use a tree-based machine learning algorithm to predict a plurality of survival rates, and wherein each one of the predicted survival rates is associated with using a different one of the VADs to treat a patient; and
adjusting a hyper-parameter of the tree-based machine learning algorithm to improve both a cross-validation score and a training score.

2. The method of claim 1, further comprising:
using the trained prediction model to select one of the VADs for the patient.

3. The method of claim 2, wherein the selected VAD is associated with a highest one of the predicted survival rates.

4. The method of claim 1, wherein the hyper-parameter is adjusted to maximize both the cross-validation score and the training score.

5. The method of claim 1, wherein the hyper-parameter is tree depth.

6. The method of claim 5, wherein the tree depth is greater than three.

7. The method of claim 5, wherein the tree depth is less than twelve.

8. The method of claim 5, wherein the tree depth is six.

9. The method of claim 1, wherein the tree-based machine learning algorithm is a bagging and random forest algorithm or a classification decision tree algorithm.

10. The method of claim 1, wherein the patient data comprises patient demographics and treatment data, wherein the patient demographics comprise gender, age, or region, and wherein the treatment data comprises duration of support, indication for use, insertion site, or ejection fraction.

11. The method of claim 1, wherein each one of the VADs is configured to be percutaneously inserted into a heart and to run in parallel with the heart to supplement cardiac output.

12. A system comprising:
one or more processors configured to use a trained prediction model to select one of a plurality of ventricular assist devices (VADs) for a patient,
wherein the prediction model is trained with training data from a data repository, wherein the training data comprises patient data and operational parameters of the VADs, and wherein the data repository comprises data from treatment of acute myocardial infarction (AMI) patients, high-risk percutaneous coronary interventions (PCI) patients, or patients in cardiogenic shock, and
wherein the trained prediction model is configured to use a tree-based machine learning algorithm to predict a plurality of survival rates, wherein each one of the predicted survival rates is associated with using a different one of the VADs to treat the patient, and wherein a hyper-parameter of the tree-based machine learning algorithm is selected to improve both a cross-validation score and a training score.

13. The system of claim 12, wherein the selected VAD is associated with a highest one of the predicted survival rates.

14. The system of claim 12, wherein the hyper-parameter is selected to maximize both the cross-validation score and the training score.

15. The system of claim 14, wherein the hyper-parameter is tree depth.

16. The system of claim 15, wherein the tree depth is between three and twelve.

17. The system of claim 12, wherein the tree-based machine learning algorithm is a bagging and random forest algorithm or a classification decision tree algorithm.

18. The system of claim 12, wherein the patient data comprises patient demographics and treatment data, wherein the patient demographics comprise gender, age, or region, and wherein the treatment data comprises duration of support, indication for use, insertion site, or ejection fraction.

19. The system of claim 12, wherein each one of the VADs is configured to be percutaneously inserted into a heart and to run in parallel with the heart to supplement cardiac output.

20. A non-transitory computer readable storage medium having instructions stored thereon that, when executed by one or more processors, cause the one or more processors to:
use a trained prediction model to select one of a plurality of ventricular assist devices (VADs) for a patient,
wherein the prediction model is trained with training data from a data repository, wherein the training data comprises patient data and operational parameters of the VADs, and wherein the data repository comprises data from treatment of acute myocardial infarction (AMI) patients, high-risk percutaneous coronary interventions (PCI) patients, or patients in cardiogenic shock, and
wherein the trained prediction model is configured to use a tree-based machine learning algorithm to predict a plurality of survival rates, wherein each one of the predicted survival rates is associated with using a different one of the VADs to treat the patient, and wherein a hyper-parameter of the tree-based machine learning algorithm is selected to improve both a cross-validation score and a training score.

* * * * *